United States Patent
Itoh et al.

(10) Patent No.: US 7,161,022 B2
(45) Date of Patent: Jan. 9, 2007

(54) PROCESS FOR PRODUCING 4-PHENYL-4-OXO-2-BUTENOIC ESTER DERIVATIVE

(75) Inventors: Isamu Itoh, Kanagawa (JP); Taichi Shintou, Kanagawa (JP)

(73) Assignees: Fujifilm Finechemicals Co., Ltd., Tokyo (JP); Meiji Seika Kaisha, Ltd., Tokyo (JP)

( * ) Notice: Subject to any disclaimer, the term of this patent is extended or adjusted under 35 U.S.C. 154(b) by 83 days.

(21) Appl. No.: 10/513,332

(22) PCT Filed: May 14, 2003

(86) PCT No.: PCT/JP03/06015

§ 371 (c)(1),
(2), (4) Date: Nov. 12, 2004

(87) PCT Pub. No.: WO03/097568

PCT Pub. Date: Nov. 27, 2003

(65) Prior Publication Data

US 2005/0176994 A1    Aug. 11, 2005

(30) Foreign Application Priority Data

May 15, 2002 (JP) ............... 2002-140411
Jun. 20, 2002 (JP) ............... 2002-180162

(51) Int. Cl.
*C07C 69/76* (2006.01)
*C07C 69/95* (2006.01)

(52) U.S. Cl. ....................................... 560/53

(58) Field of Classification Search ................... 560/53
See application file for complete search history.

(56) References Cited

U.S. PATENT DOCUMENTS

| | | | | |
|---|---|---|---|---|
| 4,473,583 A | * | 9/1984 | Bianchi et al. | 514/555 |
| 5,264,611 A | * | 11/1993 | Yanagida et al. | 560/51 |
| 6,048,896 A | * | 4/2000 | Giordani et al. | 514/545 |

FOREIGN PATENT DOCUMENTS

| | | |
|---|---|---|
| JP | 52-39020 | 10/1977 |
| JP | 55-36434 | 3/1980 |
| JP | 62-103042 | 5/1987 |
| JP | 63-130564 | 6/1988 |
| JP | 2-10816 | 3/1990 |
| JP | 4-235142 | 8/1992 |
| WO | 97/17316 | 5/1997 |

OTHER PUBLICATIONS

Grace Potter Rice, The Isomeric Esters of Para-Ethoxy-Benzoylacrylic acid, JACS vol. 46 No. 10 Oct. 1924; pp. 2319-2326.*
John A Dean, Lande's Handbook of Chemistry, Fifteenth Edition (1999) McGraw-Hill, Inc.*
D. Papa et al., J. Am. Chem. Soc., vol. 70, pp. 3356-3361, 1948.
English Language Abstract of JP 62-103042.
English Language Abstract of JP 63-130564.
English Language Abstract of JP 04-235142.
English Language Abstract of JP 55-36434.
Horii et al., *Chemicals & Pharmaceutical Bulletin* 16(7):1251-1261, 1968, XP008062413.
D. Papa et al., J. Am. Chem. Soc., vol. 70, pp. 3356-3361, 1948.
English Language Abstract of JP 62-103042. May 13, 1987 Ueda et al.
English Language Abstract of JP 63-130564. Jun. 2, 1988 Keda Tatsumi et al.
English Language Abstract of JP 04-235142. Aug. 24, 1992 Kanega Fuchi; Yamagida et al.
English Language Abstract of JP 55-36434. Mar. 14, 1980 Jojima et al.

* cited by examiner

*Primary Examiner*—Samuel A Barts
*Assistant Examiner*—Lalitha Nagubandi
(74) *Attorney, Agent, or Firm*—Greenblum & Bernstein, P.L.C.

(57) ABSTRACT

A 4-phenyl-4-oxo-2-butenoate derivative is stably supplied in a short period of time, at low cost, in high purity and on an industrial scale by a process for producing the 4-phenyl-4-oxo-2-butenoate derivative, which comprises simultaneously or continuously reacting a sulfuric ester, an aromatic hydrocarbon and a maleic anhydride derivative.

6 Claims, No Drawings

PROCESS FOR PRODUCING 4-PHENYL-4-OXO-2-BUTENOIC ESTER DERIVATIVE

TECHNICAL FIELD

The present invention relates to a process for producing a 4-phenyl-4-oxo-2-butenoate derivative which is an important intermediate for producing medicines, pesticides, perfumes, and the like.

BACKGROUND ART

4-Phenyl-4-oxo-2-butenoate derivatives are useful in the fields of medicines, pesticides, perfumes, and the like and particularly are important key compounds as intermediates for medicines. Various processes for producing the derivatives have been reported and, for example, a process for esterification of 4-phenyl-4-oxo-2-butenoic acid (JP-A-62-103042 and JP-A-63-130564) has been disclosed. In this process, however, 4-phenyl-4-oxo-2-butenoic acid derivatives as starting materials are not commercially available and are difficult to obtain. In the case of synthesizing the starting material 4-phenyl-4-oxo-2-butenoic acid derivatives, Friedel-Crafts reaction of aromatic compounds using maleic anhydride and aluminum chloride (J. Am. Chem. Soc., 70, 3356 (1948)) and the like have been known but the reaction takes a long period of time. Moreover, in the work-up after completion of the reaction, since both of the aimed 4-Phenyl-4-oxo-2-butenoic acid derivative and aluminum hydroxide are contained in an aqueous layer, separation thereof requires a special operation such as steam distillation and hence it is very difficult to conduct the operation on an industrial scale. Aldol condensation of an acetophenone with glyoxylic acid (JP-B-52-39020) or the like process has also been reported but this case also requires a long period of time for the reaction and operations are complicated. Furthermore, in these processes, it is necessary to esterify the 4-phenyl-4-oxo-2-butenoic acid derivative in a next step and the yield of the aimed 4-phenyl-4-oxo-2-butenoate derivative is very low, so that the processes are industrially not useful.

As the other process, a process of azeotropic dehydration of an aryl methyl ketone and a glyoxylic alkyl ester alkyl acetal under heating in the presence of an acid (JP-A-4-235142) has been reported. However, the glyoxylic alkyl ester alkyl acetal is very expensive and stable supply thereof on an industrial scale is also problematic.

In addition, Friedel-Crafts acylation of an aromatic hydrocarbon with a dicarboxylic acid monoester halide in the presence of an acidic catalyst (JP-A-2-10816) has also been reported. However, the process has defects that the dicarboxylic acid monoester halide is difficult to obtain, control is difficult owing to a low yield at the synthesis and a formation of a large amount of by-products, stable supply on an industrial scale is also problematic, and the like.

DISCLOSURE OF THE INVENTION

An object of the invention is to provide a production process capable of stably supplying a 4-phenyl-4-oxo-2-butenoate derivative useful as an intermediate for medicines, pesticides, perfumes, and the like, at low cost, in high purity and on an industrial scale.

As a result of the extensive studies for achieving the above object, the present inventors have found the following process and thus accomplished the invention. Namely, the invention comprises the following constitution.

1. A process for producing a 4-phenyl-4-oxo-2-butenoate derivative represented by the following general formula (III) or (IV), which comprises simultaneously or continuously reacting an aromatic hydrocarbon represented by the following general formula (I) and a maleic anhydride derivative represented by the following general formula (II) in the presence of an acid catalyst and an alkylating agent:

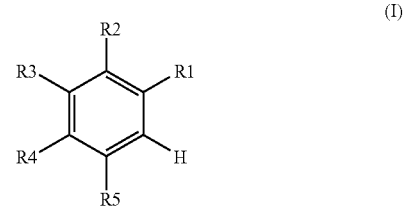

(I)

wherein R1 to R5 each independently represents a hydrogen atom, an electron-donating group, or an electron-withdrawing group, and adjacent groups of R1 to R5 may be combined to form a ring;

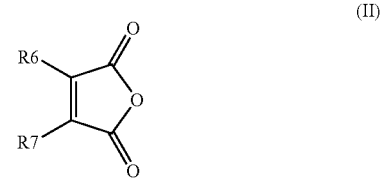

(II)

wherein R6 or R7 each independently represents a hydrogen atom, an alkyl group, an alkenyl group, an alkynyl group, an aryl group, an alkoxy group, an aryloxy group, a carbonyl group, a sulfonyl group, a carbonyloxy group, a carbonylamino group, a sulfonylamino group, an amino group, a cyano group, an alkylthio group, an arylthio group, a heterocyclic residual group, or a halogen atom, and R6 and R7 may be combined to form a partially saturated ring, an aromatic ring, or a heterocyle;

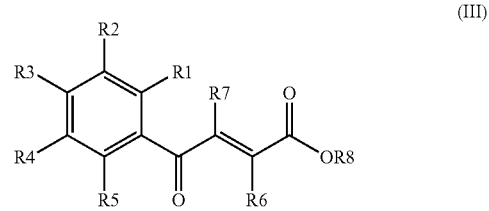

(III)

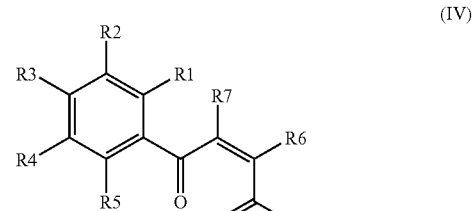

(IV)

wherein R1 to R7 have the same meanings as above and R8 represents an alkyl group.

2. The process for producing the 4-phenyl-4-oxo-2-butenoate derivative according to the above 1., wherein R1 to R5 in the above general formula (I) each independently is a hydrogen atom or an electron-donating group.

3. The process for producing the 4-phenyl-4-oxo-2-butenoate derivative according to the above 1., wherein the above general formula (I) has at least one electron-donating group and at least one electron-withdrawing group, and the total of Hammett's substituent constant σ values of R1 to R5 is 0 or more.

4. The process for producing the 4-phenyl-4-oxo-2-butenoate derivative according to any one of the above 1. to 3., wherein the electron-donating group for R1 to R5 in the above general formula (I) is a group in which a heteroatom intervenes.

5. The process for producing the 4-phenyl-4-oxo-2-butenoate derivative according to any one of the above 1. to 4., wherein the acid catalyst is aluminum chloride.

6. The process for producing the 4-phenyl-4-oxo-2-butenoate derivative according to any one of the above 1. to 5., wherein the alkylating agent is a sulfuric ester.

7. The process for producing the 4-phenyl-4-oxo-2-butenoate derivative according to any one of the above 1. to 6., which is used for producing a 4-phenyl-2-butene-1,4-dione derivative represented by the following general formula (V) or (VI):

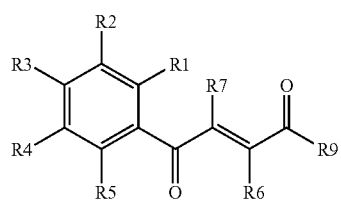

(V)

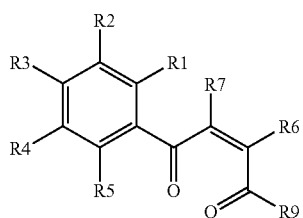

(VI)

wherein R1 to R7 have the same meanings as above and R9 represents a hydrogen atom, an alkyl group, an aryl group, a hydroxyl group, an amino group, or a hydroxylamino group.

The following will describe the invention in further detail.

The invention is in the category of Friedel-Crafts reaction.

First, one embodiment of the invention is described in detail but scope of the invention is by no means limited thereto.

In the presence of an acid catalyst and an alkylating agent, the reaction of an aromatic hydrocarbon (I) and a maleic anhydride derivative (II) proceeds according to the following scheme to form a 4-phenyl-4-oxo-2-butenoate derivative (III) or (IV).

Furthermore, the invention enables facile production of aimed compounds in one step.

In the invention, simultaneous or continuous addition of each component means that those components are subjected to a reaction in the same reaction system without changing the reaction system by conducting, for example, extraction, crystallization, or the like.

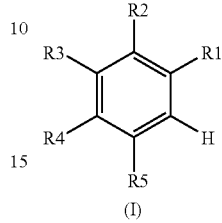

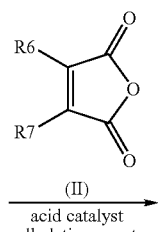

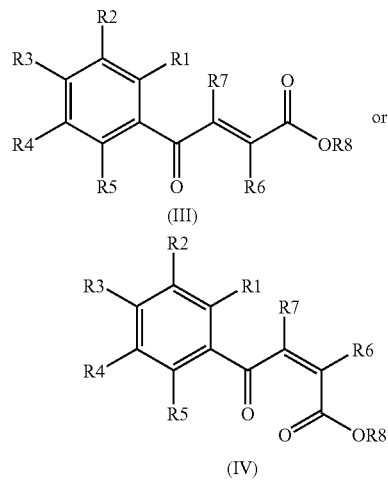

wherein

R1 to R5 each independently represents a hydrogen atom, an electron-donating group, or an electron-withdrawing group or adjacent groups of R1 to R5 may be combined to form a ring;

R6 and R7 each independently represents a hydrogen atom, an alkyl group, an alkenyl group, an alkynyl group, an aryl group, an alkoxy group, an aryloxy group, a carbonyl group, a sulfonyl group, a carbonyloxy group, a carbonylamino group, a sulfonylamino group, an amino group, a cyano group, an alkylthio group, an arylthio group, a heterocyclic residual group, and a halogen atom or R6 and R7 may be combined to form a partially saturated ring, an aromatic ring, or a heterocyle; and R8 represents an alkyl group.

The following may be conceivable as a reaction mechanism of the invention. First, a reaction mechanism of the conventional process is explained with reference to an example of E-form (E)-4-phenyl-4-oxo-2-butenoate derivative using aluminum chloride as an acid catalyst. In the reaction system, the maleic anhydride derivative and aluminum chloride are in an equilibrium state and the equilibrium is shifted to a state where the maleic anhydride derivative is ring-closed. Therefore, the amount of acyl cation formed in the system is small and hence formation of 4-phenyl-4-oxo-2-butenoic acid is very slow. Moreover, in the conventional process, further esterification should be conducted in order to obtain an aimed 4-phenyl-4-oxo-2-butenoate.

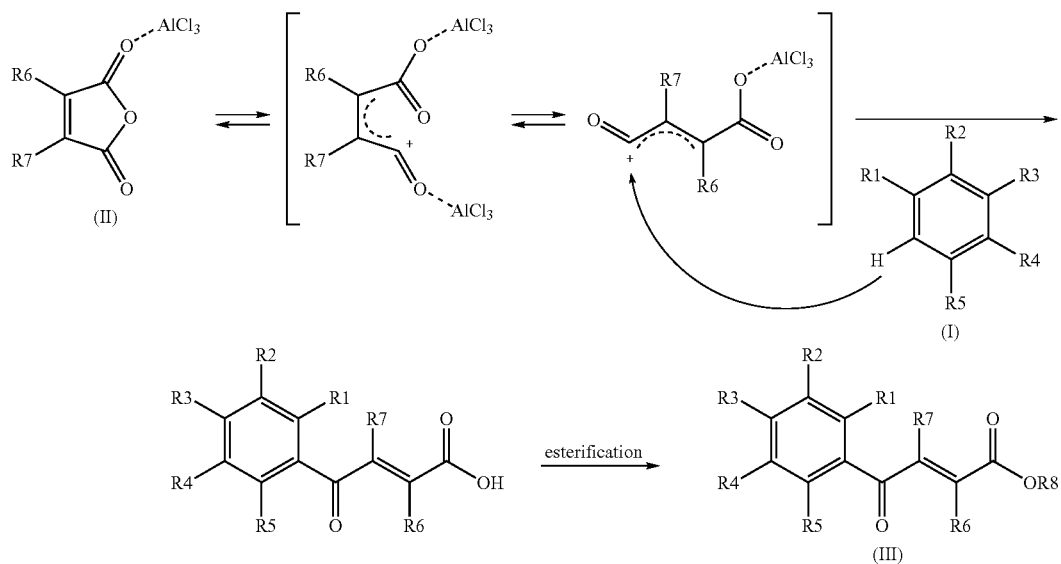

wherein R1 to R8 have the same meanings as above.

Next, one example of the invention will be described wherein diethyl sulfate is used as an alkylating agent. In the case that an alkylating agent is added like the invention, namely, in the case that diethyl sulfate is present at the time of ring-opening of the maleic anhydride derivative, the maleic anhydride derivative reacts with the ethyl group of diethyl sulfate and is converted into ethyl maleate, which is a state difficult to eliminate. As a result, it is conceivable that the equilibrium disappears, ring-closure of maleic acid does not occur, a lot of acyl cations are formed in the system, and hence the reaction proceeds. As the reaction proceeds, the acyl cations are consumed and the equilibrium between ring-opening and ring-closure of the maleic anhydride derivative is further shifted to the direction of ring-opening, i.e., the direction of acyl cation formation, so that the reaction is increasingly accelerated. As a result, it is conceivable that the reaction rate in the invention is remarkably high. In the invention, the same effect is also obtained in the case of Z-form (Z)-4-phenyl-4-oxo-2-butenoate derivative.

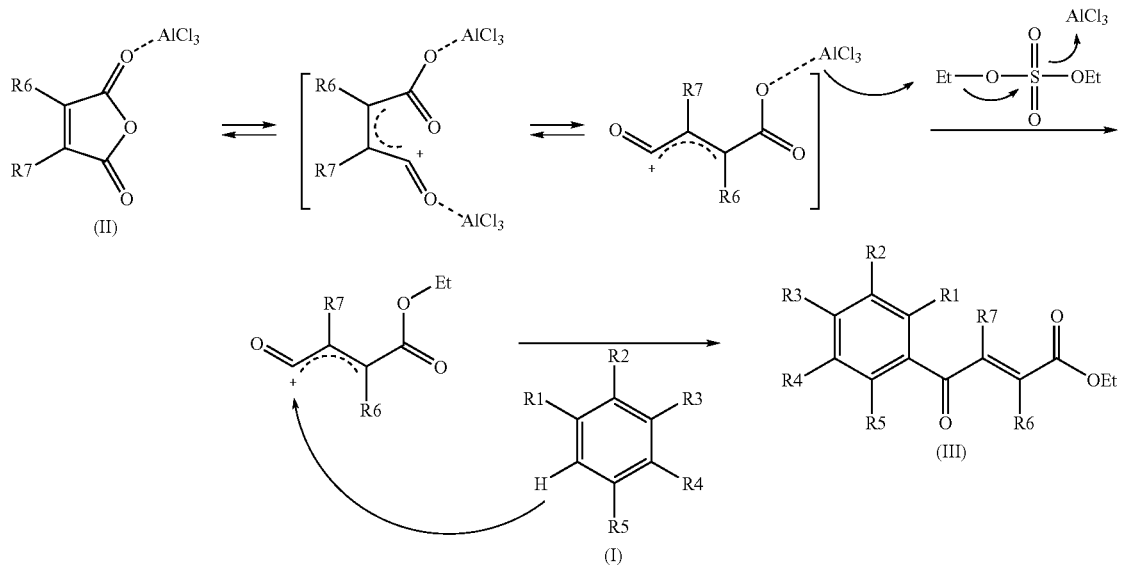

In the compound represented by the general formula (I), R1 to R5 each independently represents a hydrogen atom, an electron-donating group, or an electron-withdrawing group. Preferably, at least one of R1 to R5 is an electron-donating group.

The electron-donating group is not particularly limited as far as it is a substituent having an electron-donating action and examples thereof include linear alkyl groups such as methyl, ethyl, n-octyl, and n-dodecyl; branched alkyl groups such as i-propyl, tert-butyl, and iso-decyl; cyclic alkyl groups such as cyclopentyl and cyclohexyl; alkenyl groups such as vinyl, allyl, butenyl, and pentenyl; alkynyl groups such as ethynyl, 1-propynyl, and 1-butynyl; aryl groups such as phenyl and naphthyl; alkoxy groups such as methoxy, ethoxy, tert-butoxy, n-hexyloxy, and n-dodecyloxy; aryloxy groups such as phenoxy and naphthyloxy; hydroxyl group; monosubstituted amino groups such as methylamino, ethylamino, n-hexylamino, and phenylamino; disubstituted amino groups such as N,N-dimethylamino, N,N-diethylamino, N,N-dioctylamino, and N,N-diphenylamino; carbonylamino groups such as acetylamino, tert-butylcarbonylamino, and benzoylamino; sulfonylamino groups such as ethylsulfonylamino, n-dodecylsulfonylamino, and phenylsulfonylamino; alkylthio groups such as ethylthio, n-hexylthio, and iso-tetradecylthio; arylthio groups such as phenylthio and naphthylthio; and the like. Among these electron-donating groups, groups in which a heteroatom intervenes may be preferably mentioned and specifically, alkoxy groups, alkylthio groups, monosubstituted amino groups, and disubstituted amino groups may be mentioned. Among them, alkoxy groups are more preferred and a methoxy group and an ethoxy group are especially preferred.

The electron-withdrawing group is not particularly limited as far as it is a substituent having an electron-withdrawing action and examples thereof include halogen atoms such as chlorine, bromine, and iodine; a nitro group; a cyano group; fluoroalkyl groups such as trifluoromethyl; sulfonyl groups such as methylsulfonyl, iso-propylsulfonyl, and phenylsulfonyl; carbonyl groups such as acetyl, n-hexylcarbonyl, benzoyl, and naphthoyl; carbamoyl groups such as carbamoyl, N-phenylcarbamoyl, and N,N-diethylcarbamoyl; sulfamoyl groups such as sulfamoyl, N-methylsulfamoyl, and N,N-diethylsulfamoyl; heterocyclic residual groups such as 2-pyridyl and 4-pyridyl; and the like. Among these electron-withdrawing groups, there may be preferably mentioned halogen atoms, carbamoyl groups, sulfamoyl groups, and the like, and more preferred are halogen atoms.

These electron-donating groups and electron-withdrawing groups may further have substituent(s) and the substituent is not particularly limited unless it does not participate in the reaction.

Moreover, adjacent groups of R1 to R5 may be combined to form a ring. Specifically, there may be mentioned cyclobutane, cyclopentane, cyclohexane, 1,3-dioxolane, 1,3-oxazolane, 1,3-oxazolan-2-one, 2-pyrrolidinone, and the like.

In the combinations of R1 to R5, R1 to R5 each is preferably a hydrogen atom or an electron-donating group.

Moreover, in the combinations of R1 to R5, combinations where they have at least one electron-donating group and at least one electron-withdrawing group are also preferred. The combinations in this case are not particularly limited as far as the total of Hammett's substituent constant σ values of R1 to R5 is 0 or more, and examples thereof include alkoxy group(s) and halogen atom(s), alkoxy group(s) and sulfamoyl group(s), alkoxy group(s) and carbamoyl group(s), and the like. Preferred are combinations where the total of Hammett's substituent constant σ values of R1 to R5 is 0.5 or more.

In the compound represented by the general formula (II), R6 and R7 each independently represents specifically a hydrogen atom; a linear alkyl group such as methyl, ethyl, n-octyl, or n-dodecyl; a branched alkyl group such as i-propyl, tert-butyl, or iso-decyl; a cyclic alkyl group such as cyclopentyl or cyclohexyl; an alkenyl group such as vinyl, allyl, butenyl, or pentenyl; an alkynyl group such as ethynyl, 1-propynyl, or 1-butynyl; an aryl group such as phenyl or naphthyl; an alkoxy group such as methoxy, ethoxy, tert-butoxy, n-hexyloxy, or n-dodecyloxy; an aryloxy group such as phenoxy or naphthyloxy; a carbonyl group such as acetyl, n-hexylcarbonyl, benzoyl, naphthoyl, methoxycarbonyl, 1-octyloxycarbonyl, or phenoxycarbonyl; a sulfonyl group such as methylsulfonyl, iso-propylsulfonyl, or phenylsulfonyl; a carbamoyl group such as carbamoyl, N-phenylcarbamoyl, or N,N-diethylcarbamoyl; a sulfamoyl group such as sulfamoyl, N-methylsulfamoyl, or N,N-diethylsulfamoyl; a carbonyloxy group such as acetyloxy, n-octylcarbonyloxy, or benzoyloxy; a carbonylamino group such as acetylamino, tert-butylcarbonylamino, or benzoylamino; a sulfonylamino group such as methylsulfonylamino, n-octylsulfonylamino, or phenylsulfonylamino; an amino group such as amino, methylamino, ethylamino, n-hexylamino, phenylamino, N,N-dimethylamino, N,N-diethylamino, N,N-dioctylamino, or N,N-diphenylamino; a cyano group; an alkylthio group such as ethylthio, n-hexylthio, or iso-tetradecylthio; an arylthio group such as phenylthio or naphthylthio; a heterocyclic residual group such as 2-thienyl, 4-pyridyl, 4-pyrimidyl, or 2-furyl; a halogen atom such as chlorine, bromine, or iodine. Preferred is a hydrogen atom, an alkyl group, an aryl group, an alkoxy group, or a halogen atom and more preferred is a hydrogen atom. These groups may further have substituent(s) and the substituent is not particularly limited unless it does not participate in the reaction. Moreover, R6 and R7 may be combined to form a partially saturated ring, an aromatic ring, or a heterocyle. Specifically, there may be mentioned cyclobutene, cyclopentene, cyclohexene, benzene, pyridine, 2,3-dihydro-1,4-dithin, 1-methyl-1H-pyrrole, or the like.

In the compound represented by the general formula (III) or (IV), R8 represents an alkyl group. It is preferably a linear or branched alkyl group having 1 to 20 carbon atoms, more preferably a linear or branched alkyl group having 1 to 4 carbon atoms. These groups may further have substituent(s) and the substituent is not particularly limited unless it does not participate in the reaction.

In the compound represented by the general formula (V) or (VI), R9 represents a hydrogen atom, an alkyl group, an aryl group, a hydroxyl group, an amino group, or a hydroxylamino group. These groups may further have substituent(s) and the substituent is not particularly limited unless it does not participate in the reaction.

As the acid catalyst for use in the invention, any one can be used as far as it is used for Friedel-Crafts reaction. Specifically, there may be mentioned aluminum chloride, boron trifluoride, bismuth chloride, zinc chloride, ferric chloride, ferric sulfate, iron oxide, antimony pentachloride, gallium chloride, indium chloride, stannic chloride, titanium tetrachloride, hydrochloric acid, hafnium triflate, scandium triflate, copper triflate, polyphosphoric acid, iodine, lithium perchlorate, sulfuric acid, p-toluenesulfonic acid, methanesulfonic acid, trifluoromethanesulfonic acid, fluorosulfonic acid, zeolite β, zeolite H—Y, Nafion-H, ionic liquids (e.g., 1-ethyl-3-methyl-1H-imidazolium tetrachloroaluminium salt, 1-ethyl-3-methyl-1H-imidazolium hexafluoroantimonium salt, 1-ethyl-3-methyl-1H-imidazolium trifluoromethanesulfonium salt, 1-butyl-3-methyl-1H-imidazolium-tetrachloroaluminium salt, 1-butyl-3-methyl-1H-imidazolium hexafluorophosphonium salt, 1-butyl-2,3-dimethyl-1H-imidazolium tetrachloroaluminium salt, etc.), and the like. Preferred are aluminum chloride, stannic chloride, boron trifluoride, bismuth chloride, ferric chloride, hafnium triflate, scandium triflate, zeolite β, zeolite H—Y, and ionic liquids and more preferred is aluminum chloride.

The amount of the acid catalyst for use in the invention is not limited as far as the amount is 0.01 mol or more per mol of the aromatic hydrocarbon represented by the general formula (I). The amount is preferably from 1.0 mol to 10.0 mol, more preferably from 2.0 to 3.5 mol in the case of aluminum chloride, and the amount is preferably from 0.01 to 0.5 mol, more preferably from 0.02 to 0.2 mol in the case of the other acid catalysts.

A variety of the alkylating agents for use in the invention are offered commercially and easily available and they can be used as they are. Specifically, the following may be mentioned.

1) Alkyl halides: chlorobutyl, bromomethyl, bromoethyl, bromopropyl, bromobutyl, methyl iodide, ethyl iodide, propyl iodide, butyl iodide, etc.
2) Sulfuric esters: methyl sulfate, ethyl sulfate, propyl sulfate, butyl sulfate, dimethyl sulfate, diethyl sulfate, dipropyl sulfate, dibutyl sulfate, etc.
3) Sulfonic esters: methyl benzenesulfonate, ethyl benzenesulfonate, propyl benzenesulfonate, butyl benzenesulfonate, methyl p-toluenesulfonate, ethyl p-toluenesulfonate, propyl p-toluenesulfonate, butyl p-toluenesulfonate, pentyl p-toluenesulfonate, hexyl p-toluenesulfonate, heptyl p-toluenesulfonate, octyl p-toluenesulfonate, octadecyl p-toluenesulfonate, 2-methylbutyl p-toluenesulfonate, 2-methoxyethyl p-toluenesulfonate, methyl methanesulfonate, ethyl methanesulfonate, propyl methanesulfonate, butyl methanesulfonate, methyl trifluoromethanesulfonate, ethyl trifluoromethanesulfonate, propyl trifluoromethanesulfonate, butyl trifluoromethanesulfonate, etc.
4) Sulfurous esters: dimethyl sulfite, diethyl sulfite, dipropyl sulfite, dibutyl sulfite, etc.
5) Phosphoric esters: trimethyl phosphate, triethyl phosphate, tripropyl phosphate, tributyl phosphate, trioctyl phosphate, tris(2-ethylhexyl)phosphate, tris(2-chloroethyl) phosphate, tris(2-chloro-1-methylethyl) phosphate, dimethyl phosphate, diethyl phosphate, dipropyl phosphate, dibutyl phosphate, etc.
6) Phosphorous esters: trimethyl phosphite, triethyl phosphite, tripropyl phosphite, tributyl phosphite, dimethyl phosphite, diethyl phosphite, dipropyl phosphite, dibutyl phosphite, dilauryl phosphite, etc.
7) Carbonic esters: dimethyl carbonate, diethyl carbonate, dipropyl carbonate, dibutyl carbonate, etc.
8) Boric esters: trimethyl borate, triethyl borate, tripropyl borate, tributyl borate, etc.
9) Ortho acid esters: methyl orthoformate, ethyl orthoformate, propyl orthoformate, butyl orthoformate, trimethyl orthoacetate, triethyl orthoacetate, tripropyl orthoformate, tributyl orthoformate, triethyl orthopropionate, diethylphenyl orthoformate, trimethyl orthovalerate, tetraethyl orthosilicate, tetrabutyl orthosilicate, tetramethyl orthotitanate, tetraethyl orthotitanate, tetrapropyl orthotitanate, tetrabutyl orthotitanate, etc.

Preferably, sulfuric esters and sulfonic esters may be mentioned. Among them, preferred are dimethyl sulfate, diethyl sulfate, methyl benzenesulfonate, ethyl benzenesulfonate, methyl p-toluenesulfonate, ethyl p-toluenesulfonate, methyl methanesulfonate, ethyl methanesulfonate, methyl trifluoromethanesulfonate, and ethyl trifluoromethanesulfonate. Particularly preferred are sulfuric esters and most preferred is diethyl sulfate.

The amount of the alkylating agent to be used is not limited as far as the amount is 0.5 mol or more per mol of the aromatic hydrocarbon represented by the general formula (I). The alkylating agent is used in the range of usually from 0.5 to 20 mol, preferably from 1.0 mol to 10.0 mol, more preferably from 1.2 to 3.5 mol.

The amount of the maleic anhydride derivative represented by the general formula (II) for use in the invention is not limited as far as the amount is 1 mol or more per mol of the aromatic hydrocarbon represented by the general formula (I). The maleic anhydride derivative is used in the range of usually from 1.1 to 20 mol, preferably from 1.5 mol to 10.0 mol, more preferably from 2.0 to 5.0 mol.

In the invention, a reaction accelerator may be used or may not be used but the reaction accelerator is preferably added in order to obtain the aimed compound in a short period of time and in high yields. As the reaction accelerator, there may be mentioned halogen compounds such as copper iodide, potassium iodide, iodine, copper bromide, and copper chloride; quaternary ammonium salts such as tetra(n-butyl)ammonium iodide and tetra(n-butyl)ammonium bromide; and nitrile compounds such as acetonitrile, propionitrile, and benzonitrile. Preferred are copper iodide, tetra(n-butyl)ammonium iodide, and acetonitrile, and more preferred are copper iodide and acetonitrile.

The amount of the above reaction accelerator to be used is in the range of 0.001 to 0.1 mol, preferably 0.001 to 0.05 mol, more preferably 0.001 to 0.01 mol per mol of the aromatic hydrocarbon represented by the general formula (I). In the case of a nitrile compound, the accelerator is used in the range of 0.001 to 2 mol, preferably 0.001 to 1 mol, more preferably 0.01 to 0.6 mol per mol of the aromatic hydrocarbon represented by the general formula (I).

In the invention, a reaction solvent may be used or may not be used but usually, any one can be used as far as it is inert to the reaction. The following may be mentioned as solvents inert to usual Friedel-Crafts reaction.

(i) Aromatic hydrocarbon compounds having an electron-withdrawing group: chlorobenzene, dichlorobenzene, trichlorobenzene, bromobenzene, dibromobenzene, nitrobenzene, etc.
(ii) Aliphatic halogenated hydrocarbon compounds: dichloromethane, chloroform, carbon tetrachloride, dibromomethane, 1,2-dichloroethane, etc.
(iii) Aliphatic nitrated hydrocarbon compounds: nitromethane, nitroethane, etc.
(iv) Ionic liquids: 1-ethyl-3-methyl-1H-imidazolium tetrachloroaluminium salt, 1-ethyl-3-methyl-1H-imidazolium hexafluorophosphonium salt, 1-ethyl-3-methyl-1H-imidazolium hexafluoroantimonium salt, 1-butyl-3-methyl-1H-imidazolium hexafluorophosphonium salt, 1-ethyl-3-methyl-1H-imidazolium trifluoromethanesulfonium salt, methylimidazolium bis(trifluoromethanesulfone)imide salt, 1,2-dimethyl-3-propylimidazolium hexafluorophosphonium salt, trimethylpropylammonium tetrafluoroborate salt, tetra-n-butylphosphonium bromide, etc.

These solvents can be used solely or in combination of two or more of them as a reaction solvent. Among the above solvents, preferred are chlorobenzene, nitrobenzene, dichloromethane, chloroform, and 1,2-dichloroethane, and more preferred are chlorobenzene and dichloromethane. By the use of these solvents, the reaction is completed in a short period of time and the aimed compound is obtained in high yields.

The amount of the reaction solvent to be used is in the range of usually 1 to 1000 ml, preferably 5 to 500 ml, more preferably 35 to 150 ml per 0.1 mol of the aromatic hydrocarbon represented by the general formula (I).

The reaction is carried out at a temperature of the range of usually −20 to 150° C., preferably 0 to 80° C., more preferably 5 to 50° C. The reaction is completed within a reaction time of usually 1 to 10 hours, more preferably 1 to 4 hours.

After completion of the reaction, the acid catalyst is decomposed or filtrated and then the organic layer is neutralized with a base such as sodium hydrogen carbonate to remove excess maleic anhydride derivative. Furthermore, after the solvent is concentrated under reduced pressure, a highly pure 4-phenyl-4-oxo-2-butenoate derivative can be obtained by crystallization with adding an alcohol, hexane, or the like.

Furthermore, the invention is particularly effective as a process for producing an intermediate for the synthesis of compounds easily derived by functional group conversion of conventional ester derivatives, such as 4-phenyl-4-oxo-2-butenamides, 4-phenyl-4-oxo-2-butenoic acids, 4-phenyl-4-oxo-2-butenehydroxamic acids, and 4-phenyl-2-butene-1,4-diones. After a 4-phenyl-4-oxo-2-butenoate derivative is obtained according to the invention, these compounds can be derived directly in the reaction system or, after once isolated, using various conventional methods. Incidentally, these compounds are not limited to the above.

EXAMPLES

The following will explain the present invention more specifically with reference to Examples but the invention is not limited thereto. Evaluation of purity in Examples was based on high performance liquid chromatography (abbreviated as HPLC). In this connection, those described as "HPLC analysis" in Examples were measured under the following conditions and when the conditions were changed, conditions therefor were described in detail.

(Measuring Conditions by HPLC Analysis)
Column: Inertsil ODS-2 φ4.6×250 mm (manufactured by GL Science)
Detecting UV wavelength: 270 nm
Eluting liquid: acetonitrile/10 mM phosphate buffer (pH 2.6)=45/55
Flow rate of eluting liquid: 1.0 ml/min
Column temperature: 40° C.

Example 1

Synthesis of ethyl (E)-4-(3,4-dimethoxyphenyl)-4-oxo-2-butenoate

Into a 500 ml four-neck flask were charged 66.9 g (0.682 mol) of maleic anhydride, 150 ml of chlorobenzene, 71.6 ml (0.546 mol) of diethyl sulfate under a nitrogen atmosphere. Then, the whole was cooled to 10° C. or lower and 67.6 g (0.507 mol) of aluminum chloride was added thereto. While temperature was maintained at 10 to 15° C., 25 ml (0.195 mol) of 1,2-dimethoxybenzene was added dropwise, followed by 4 hours of reaction. After termination of the reaction was confirmed by HPLC analysis, the reaction solution was added dropwise to 200 ml of a 1N hydrochloric acid aqueous solution cooled to 0° C. to decompose excess aluminum chloride. After liquid separation, the organic layer was washed with 200 ml of a 10% sodium bicarbonate aqueous solution to remove excess maleic anhydride. After the solvent was removed by evaporation under reduced pressure, the residue was crystallized from 5 ml of ethanol to obtain 36.2 g (yield 70.3%) of the aimed compound as light yellow crystals. As a result of HPLC analysis, the purity was found to be 99.8%.

Example 2

Synthesis was conducted under similar conditions to those in Example 1 except that 0.186 g (0.975 mmol) of copper iodide was added as a reaction accelerator.

Comparative Example 1

Synthesis of ethyl (E)-4-(3,4-dimethoxyphenyl)-4-oxo-2-butenoate

Step 1

Synthesis of (E)-4-(3,4-dimethoxyphenyl)-4-oxo-2-butenoic acid

Into a 500 ml four-neck flask were charged 66.9 g (0.682 mol) of maleic anhydride and 150 ml of chlorobenzene under a nitrogen atmosphere. Then, the whole was cooled to 10° C. or lower and 67.6 g (0.507 mol) of aluminum chloride was added thereto. While temperature was maintained at 10 to 15° C., 25 ml (0.195 mol) of 1,2-dimethoxybenzene was added dropwise, followed by 48 hours of reaction at 20 to 30° C. After termination of the reaction was confirmed by HPLC analysis, the reaction solution was added dropwise to 200 ml of a 1N hydrochloric acid aqueous solution cooled to 0° C. to decompose excess aluminum chloride. The resulting mixture was extracted with 400 ml of ethyl acetate and washing was conducted twice with 200 ml of a 1N hydrochloric acid aqueous solution. The organic layer was washed three times with 200 ml of a saturated sodium hydrogen carbonate aqueous solution to extract (E)-4-(3,4-dimethoxyphenyl)-4-oxo-2-butenoic acid into the aqueous layer, followed by adjusting the aqueous layer to pH 2.0. After 24 h of stirring at 5° C., filtration was carried out to obtain 28.6 g (yield 62.1%) of the aimed compound as light yellow crystals. As a result of HPLC analysis, the purity was found to be 96.5%.

Step 2

Synthesis of ethyl (E)-4-(3,4-dimethoxyphenyl)-4-oxo-2-butenoate

Into a 500 ml four-neck flask were charged 26.0 g (0.11 mol) of (E)-4-(3,4-dimethoxyphenyl)-4-oxo-2-butenoic acid obtained in Comparative Example 1, 260 ml of dimethylformamide (DMF), 24.7 g (0.16 mol) of diethyl sulfate, and 30.4 g (0.22 mol) of potassium carbonate under a nitrogen atmosphere, followed by 2 hours of reaction at 35 to 45° C. After completion of the reaction was confirmed by HPLC analysis, a mixed solution of 3.6 g (0.06 mol) of acetic acid/3.6 g of DMF was added dropwise and the whole was stirred at 30 to 35° C. for 1 hour to decompose excess diethyl sulfate. Extraction with a mixed solution of 400 ml of ethyl acetate/400 ml of water/23.4 g of hydrochloric acid was conducted and the organic layer was washed twice with 400 ml of water. After the solvent was removed by evaporation under reduced pressure, the residue was crystallized from 9 ml of ethanol, and 19 ml of water to obtain 25.3 g (yield 87%) of the aimed compound as light yellow crystals. The total yield from 1,2-dimethoxybenzene was 54.0% and the purity was found to be 99.6%.

Example 3

Synthesis of ethyl (E)-4-(3-chloro-4-methoxyphenyl)-4-oxo-2-butenoate

Synthesis was conducted under similar conditions to those in Example 1 except that 23.2 ml (0.195 mol) of 1-chloro-2-methoxybenzene was added dropwise instead of 25 ml (0.195 mol) of 1,2-dimethoxybenzene in Example 1. After the solvent was removed by evaporation under reduced pressure, the residue was crystallized from 5 ml of ethanol to obtain 35.7 g (yield 68.0%) of the aimed compound as light yellow crystals. As a result of HPLC analysis, the purity was found to be 99.6%.

Example 4

Synthesis was conducted under similar conditions to those in Example 3 except that 0.186 g (0.975 mmol) of copper iodide was added as a reaction accelerator.

Comparative Example 2

Synthesis of ethyl (E)-4-(3-chloro-4-methoxyphenyl)-4-oxo-2-butenoate

Step 1

Synthesis of (E)-4-(3-chloro-4-methoxyphenyl)-4-oxo-2-butenoic acid

Into a 500 ml four-neck flask were charged 66.9 g (0.682 mol) of maleic anhydride and 150 ml of chlorobenzene under a nitrogen atmosphere. Then, the whole was cooled to 10° C. or lower and 67.6 g (0.507 mol) of aluminum chloride was added thereto. While temperature was maintained at 10 to 15° C., 23.2 ml (0.195 mol) of 1-chloro-2-methoxybenzene was added dropwise, followed by 51 hours of reaction at 20 to 30° C. After termination of the reaction was confirmed by HPLC analysis, the reaction solution was added dropwise to 200 ml of a 1N hydrochloric acid aqueous solution cooled to 0° C. to decompose excess aluminum chloride. Extraction with 400 ml of ethyl acetate was conducted and the organic layer was washed twice with 200 ml of a 1N hydrochloric acid aqueous solution. Then, the organic layer was extracted three times with 200 ml of a saturated sodium hydrogen carbonate aqueous solution to extract (E)-4-(3-chloro-4-methoxyphenyl)-4-oxo-2-butenoic acid into the aqueous layer, followed by adjusting the aqueous layer to pH 2.0. After 24 hours of stirring at 5° C., filtration was carried out to obtain 28.4 g (yield 60.5%) of the aimed compound as light yellow crystals. As a result of HPLC analysis, the purity was found to be 96.3%.

Step 2

Synthesis of ethyl (E)-4-(3-chloro-4-methoxyphenyl)-4-oxo-2-butenoate

Into a 500 ml four-neck flask were charged 26.5 g (0.11 mol) of (E)-4-(3-chloro-4-methoxyphenyl)-4-oxo-2-butenoic acid obtained in Step 1, 260 ml of dimethylformamide (DMF), 24.7 g (0.16 mol) of diethyl sulfate, and 30.4 g (0.22 mol) of potassium carbonate under a nitrogen atmosphere, followed by 2 hours of reaction at 35 to 45° C. After completion of the reaction was confirmed by HPLC analysis, a mixed solution of 3.6 g (0.06 mol) of acetic acid/3.6 g of DMF was added dropwise and the whole was stirred at 30 to 35° C. for 1 hour to decompose excess diethyl sulfate. Thereafter, extraction with a mixed solution of 400 ml of ethyl acetate/400 ml of water/23.4 g of hydrochloric acid was conducted and the organic layer was washed twice with 400 ml of water. After the solvent was removed by evaporation under reduced pressure, the residue was crystallized from 9 ml of ethanol, and 19 ml of water to obtain 25.4 g (yield 86.0%) of the aimed compound as light yellow crystals. The total yield from 1-chloro-2-methoxybenzene was 52.0% and the purity was found to be 99.6%.

Results of Examples 1 to 4 and Comparative Examples 1 and 2 are shown in Table 1. In this connection, the reaction time of Comparative Examples is described as the total of those in Steps 1 and 2.

TABLE 1

| | Aromatic hydrocarbon | Reaction accelerator | Reaction time (h) | Yield (%) | Purity (%) |
|---|---|---|---|---|---|
| Example 1 | 1,2-Dimethoxybenzene | Not added | 4 | 70.3 | 99.8 |
| Example 2 | 1,2-Dimethoxybenzene | Copper iodide | 2 | 61.2 | 99.7 |
| Comparative Example 1 | 1,2-Dimethoxybenzene | Not added | Total 50 | Total 54.0 | 99.6 |
| Example 3 | 1-Chloro-2-methoxybenzene | Not added | 4 | 68.0 | 99.6 |
| Example 4 | 1-Chloro-2-methoxybenzene | Copper iodide | 2 | 64.5 | 99.8 |
| Comparative Example 2 | 1-Chloro-2-methoxybenzene | Not added | Total 53 | Total 52.0 | 99.6 |

From the results shown in Table 1, the following are apparent. By the process of the invention, it is possible to obtain aimed ethyl (E)-4-(3,4-dimethoxyphenyl)-4-oxo-2-butenoate or ethyl (E)-4-(3-chloro-4-methoxyphenyl)-4-oxo-2-butenoate in a remarkably short period of time and in high purity. On the other hand, in the cases of Comparative Examples, the reaction time is very long, i.e., 48 hours for the synthesis of (E)-4-(3,4-dimethoxyphenyl)-4-oxo-2-butenoic acid and 51 hours for (E)-4-(3-chloro-4-methoxyphenyl)-4-oxo-2-butenoic acid and, in addition, the step of ethyl esterification should be further carried out for obtaining the aimed compounds, so that the process costs very high as compared with the process of the invention and hence is not preferred as an industrial production process.

Examples 5 to 10

Synthesis was conducted under similar conditions to those in Example 1 except that the acid catalyst was changed from aluminum chloride to each of the acid catalysts shown in Table 2 in Example 1. Table 2 shows the results.

Examples 11 to 15

Synthesis was conducted under similar conditions to those in Example 3 except that the acid catalyst was changed from aluminum chloride to each of the acid catalysts shown in Table 2 in Example 3. Table 2 shows the results.

TABLE 2

| Example | Acid catalyst | Amount of acid catalyst (mol) | Reaction time (h) | Yield (%) | Purity (%) |
|---|---|---|---|---|---|
| 5 | Ferric chloride | 0.039 | 3 | 58.4 | 99.4 |
| 6 | p-Toluenesulfonic acid | 0.020 | 3 | 55.7 | 99.3 |
| 7 | Stannic chloride | 0.039 | 4 | 62.8 | 99.4 |
| 8 | Titanium tetrachloride | 0.039 | 3 | 61.0 | 99.2 |
| 9 | Zinc chloride | 0.008 | 4 | 65.9 | 99.2 |
| 10 | Iodine | 0.020 | 4 | 50.3 | 99.0 |
| 11 | 1-Ethyl-3-methyl-1H-imidazolium tetrachloroaluminium salt | 0.005 | 3 | 66.8 | 99.5 |
| 12 | Ferric chloride | 0.039 | 3 | 65.2 | 99.3 |
| 13 | Bismuth chloride | 0.020 | 3 | 55.9 | 99.3 |
| 14 | Boron trifluoride | 0.039 | 4 | 60.3 | 99.4 |
| 15 | 1-Ethyl-3-methyl-1H-imidazolium trifluoromethanesulfonium salt | 0.010 | 3 | 66.8 | 99.5 |

Examples 16 to 30

Synthesis was conducted under similar conditions to those in Example 1 except that the alkylating agent was changed from diethyl sulfate to each of the alkylating agents shown in Table 3 in Example 1. Table 3 shows the results.

Examples 31 to 37

Synthesis was conducted under similar conditions to those in Example 3 except that the alkylating agent was changed from diethyl sulfate to each of the alkylating agents shown in Table 3 in Example 3. Table 3 shows the results.

TABLE 3

| Example | Alkylating agent | Amount of Alkylating agent (mol) | Reaction time (h) | Yield (%) | Purity (%) |
|---|---|---|---|---|---|
| 16 | Bromopropyl | 0.507 | 3 | 60.4 | 99.4 |
| 17 | Iodooctadecane | 0.507 | 4 | 55.6 | 99.3 |
| 18 | Ethyl trifluoromethanesulfonate | 0.507 | 4 | 55.6 | 99.4 |
| 19 | Ethyl methanesulfonate | 0.507 | 3 | 60.9 | 99.5 |
| 20 | Diethyl sulfite | 0.507 | 4 | 68.4 | 99.2 |
| 21 | Trioctyl phosphate | 0.507 | 4 | 59.8 | 99.2 |
| 22 | Dibutyl phosphate | 0.507 | 4 | 55.6 | 99.0 |
| 23 | Trimethyl phosphite | 0.507 | 4 | 65.7 | 99.1 |
| 24 | Dilauryl phosphite | 0.507 | 4 | 65.0 | 99.2 |
| 25 | Diethyl carbonate | 0.507 | 4 | 58.1 | 98.9 |
| 26 | Trimethyl borate | 0.253 | 3 | 66.9 | 99.3 |
| 27 | Methyl orthoformate | 0.253 | 3 | 67.3 | 99.4 |
| 28 | Triethyl orthopropionate | 0.253 | 3 | 62.4 | 99.3 |
| 29 | Tetrapropyl orthotitanate | 0.253 | 3 | 64.6 | 99.0 |
| 30 | Tetraethyl orthosilicate | 0.253 | 3 | 55.8 | 99.3 |
| 31 | Methyl benzenesulfonate | 0.507 | 4 | 70.1 | 99.2 |
| 32 | Diethyl sulfate | 0.507 | 4 | 70.9 | 99.5 |
| 33 | Tris(2-chloromethyl) phosphate | 0.507 | 3 | 61.1 | 99.2 |
| 34 | Ethyl p-toluenesulfonate | 0.507 | 4 | 68.2 | 99.3 |
| 35 | Tributyl phosphite | 0.507 | 3 | 65.7 | 99.2 |
| 36 | Tripropyl borate | 0.253 | 4 | 64.7 | 99.3 |
| 37 | Triethyl orthoacetate | 0.253 | 4 | 59.8 | 98.9 |

Examples 38 to 67

Synthesis was conducted under similar conditions to those in Example 1 using each combination of the hydrocarbons, the alkylating agents, and the maleic anhydride derivatives shown in the following Table 4 instead of the combination of 1,2-dimethoxybenzene, diethyl sulfate, and maleic anhydride in Example 1. Table 4 shows the results.

TABLE 4

| Example | Aromatic hydrocarbon | Alkylating agent | Maleic anhydride derivative |
|---|---|---|---|
| 38 | 1,2-diethoxybenzene (EtO, EtO on benzene) | (EtO)$_2$SO$_2$ | maleic anhydride |
| 39 | toluene (Me on benzene) | 4-Me-C$_6$H$_4$-SO$_2$OEt | maleic anhydride |
| 40 | anisole (MeO on benzene) | 4-Me-C$_6$H$_4$-SO$_2$O(n-Bu) | maleic anhydride |

TABLE 4-continued
| | | | |
|---|---|---|---|
| 41 | 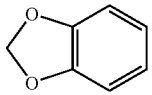 | (MeO)₂SO₂ | 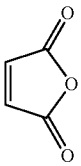 |
| 42 | 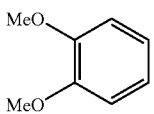 | (EtO)₂SO₂ | 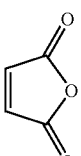 |
| 43 | 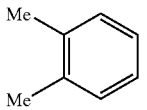 | (EtO)₂SO₂ | 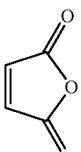 |
| 44 | 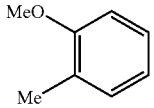 | (EtO)₂SO₂ | 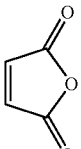 |
| 45 | 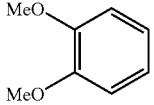 | (EtO)₂SO₂ | 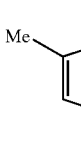 |
| 46 | 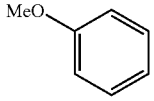 | (MeO)₂SO₂ | 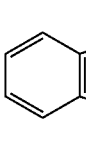 |
| 47 | 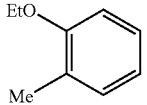 | (EtO)₂SO₂ | 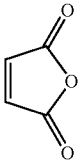 |
| 48 | 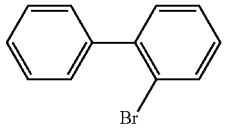 | 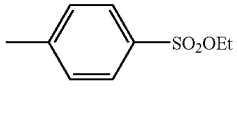—SO₂OEt | 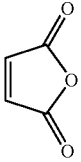 |
| 49 | 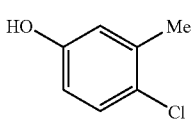 | 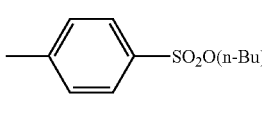—SO₂O(n-Bu) | 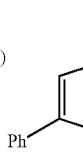 |

TABLE 4-continued

| | | | |
|---|---|---|---|
| 50 | 4-MeO-C6H4-Br | (MeO)2SO2 | 3-EtO-furan-2,5-dione |
| 51 | 3-MeS-C6H4-Cl | (EtO)2SO2 | maleic anhydride |
| 52 | 4-Cl-3-Me-5-MeO-C6H3 (2-Me, 4-Cl, 5-MeO phenyl) | (EtO)2SO2 | maleic anhydride |
| 53 | 1-chloronaphthalene | (EtO)2SO2 | maleic anhydride |
| 54 | 4-Cl-3,5-Me2-MeO-C6H2 | (EtO)2SO2 | 3-Me-furan-2,5-dione |
| 55 | 2-Cl-MeO-C6H4 | (MeO)2SO2 | phthalic anhydride |
| 56 | 2-EtO-3-MeO-C6H3-CN | (EtO)2SO2 | maleic anhydride |
| 57 | 2,3-(EtO)2-NO2-C6H3 | (MeO)2SO2 | maleic anhydride |
| 58 | 3,4-(HO)2-NO2-C6H3 | (EtO)2SO2 | maleic anhydride |

TABLE 4-continued

| # | Substrate | Reagent | Product |
|---|---|---|---|
| 59 | 2-SO₂CH₃, 3-EtO, 4-EtO benzene | (MeO)₂SO₂ | 3-Et maleic anhydride |
| 60 | 4-(2,6-dimethylphenyl)pyridine | CH₃SO₃Et | maleic anhydride |
| 61 | Et₂N-phenyl | PhSO₂OMe | maleic anhydride |
| 62 | MeHN-phenyl | 4-Me-C₆H₄-SO₂OEt | 3-Et maleic anhydride |
| 63 | 3-EtO, 1-SO₂NHMe benzene | CF₃SO₃Et | 3-Me maleic anhydride |
| 64 | 4-MeO, 1-CONEt₂ benzene | CH₃SO₃Me | maleic anhydride |
| 65 | 2-MeO, 3-MeO, 1-CONHMe benzene | CF₃SO₃Me | maleic anhydride |
| 66 | 3-EtO, 4-EtO, 1-SO₂NEt₂ benzene | CF₃SO₃Et | 3-Cl maleic anhydride |
| 67 | 3-MeO, 4-MeO, 1-Br benzene | PhSO₂OMe | maleic anhydride |

TABLE 4-continued
| Example | Product | Yield (%) | Purity (%) |
|---|---|---|---|
| 38 | 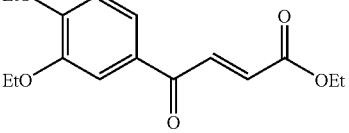 | 70.5 | 99.8 |
| 39 | 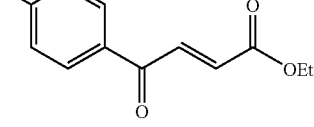 | 60.9 | 99.4 |
| 40 | 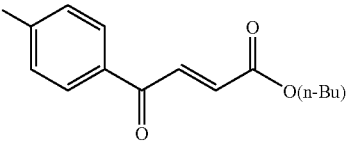 | 66.9 | 99.5 |
| 41 | 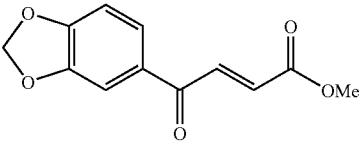 | 61.1 | 99.3 |
| 42 | 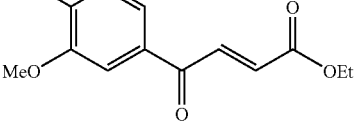 | 69.7 | 99.7 |
| 43 | 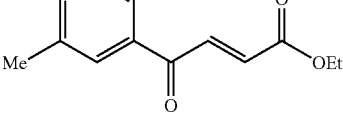 | 65.5 | 99.6 |
| 44 | 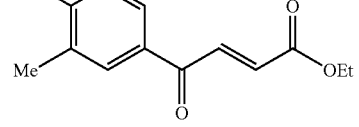 | 61.3 | 99.6 |
| 45 | 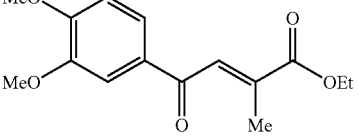 | 66.2 | 99.5 |
| 46 | 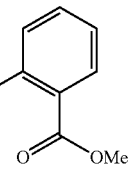 | 61.3 | 99.6 |

TABLE 4-continued

| # | Structure | Value 1 | Value 2 |
|---|---|---|---|
| 47 | (EtO, I-substituted phenyl)–C(O)–CH=CH–C(O)OEt | 65.3 | 99.5 |
| 48 | (2-bromo-biphenyl-4-yl)–C(O)–CH=CH–C(O)OEt | 62.8 | 99.4 |
| 49 | (5-chloro-2-hydroxy-4-methylphenyl)–C(O)–CH=C(Ph)–C(O)O(n-Bu) | 60.9 | 99.3 |
| 50 | (2-bromo-5-methoxyphenyl)–C(O)–CH=C(OEt)–C(O)OMe | 51.7 | 99.3 |
| 51 | (2-chloro-4-methylthiophenyl)–C(O)–CH=CH–C(O)OEt | 57.0 | 99.7 |
| 52 | (5-chloro-2-methoxy-4-methylphenyl)–C(O)–CH=CH–C(O)OEt | 62.1 | 99.6 |
| 53 | (4-chloronaphthalen-1-yl)–C(O)–CH=CH–C(O)OEt | 60.3 | 99.6 |
| 54 | (3-chloro-6-methoxy-2,4-dimethylphenyl)–C(O)–C(Me)=CH–C(O)OEt | 63.0 | 99.5 |
| 55 | (3-chloro-4-methoxyphenyl)–C(O)–(2-methoxycarbonylphenyl) | 66.4 | 99.6 |

TABLE 4-continued
| 56 | 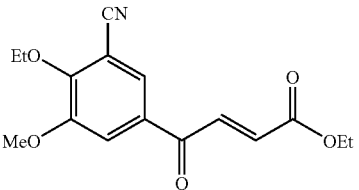 | 60.3 | 99.2 |
| --- | --- | --- | --- |
| 57 | 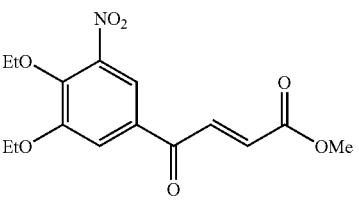 | 62.9 | 99.5 |
| 58 | 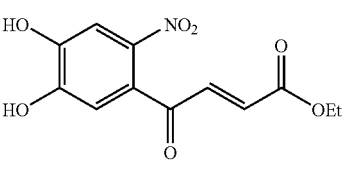 | 65.7 | 99.5 |
| 59 | 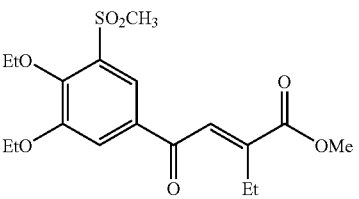 | 58.1 | 99.4 |
| 60 | 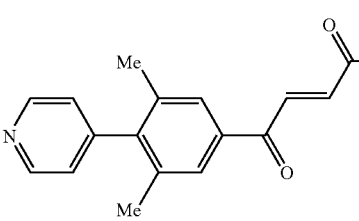 | 59.9 | 99.2 |
| 61 | 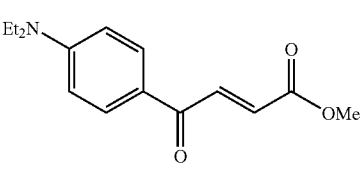 | 65.2 | 99.5 |
| 62 | 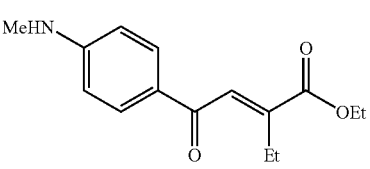 | 63.9 | 99.3 |
| 63 | 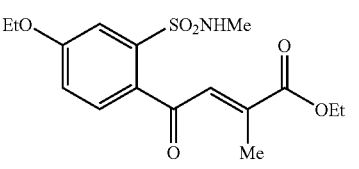 | 59.8 | 99.3 |

TABLE 4-continued
| | | | |
|---|---|---|---|
| 64 | 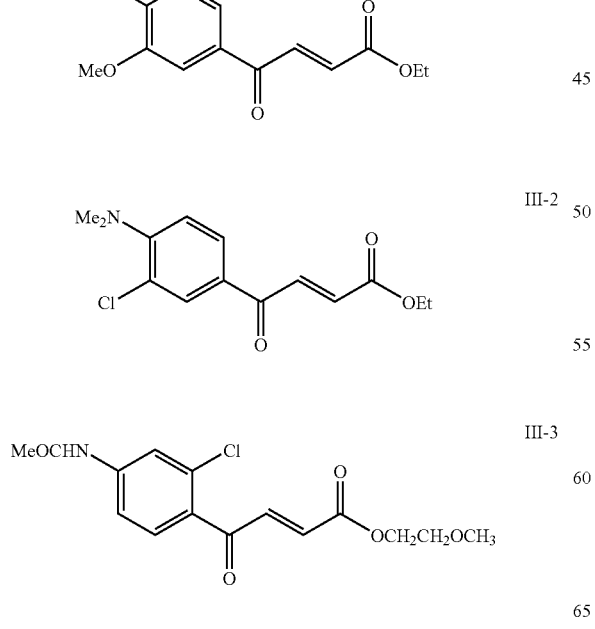 | 60.3 | 99.3 |
| 65 | | 58.1 | 99.4 |
| 66 | | 57.4 | 99.2 |
| 67 | | 58.9 | 99.5 |
Synthesis was conducted under the same conditions as in Example 3 changing the combination of 1-chloro-2-methoxybenzene and maleic anhydride in Example 3 to produce the following compounds III-1 to III-8.
III-1
III-2
III-3
III-4 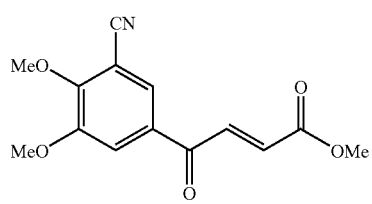
III-5 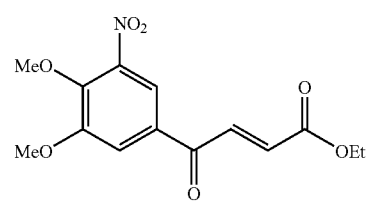
III-6 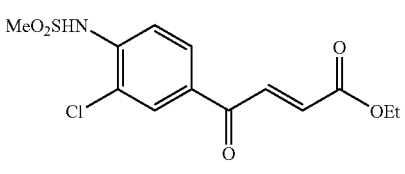
III-7 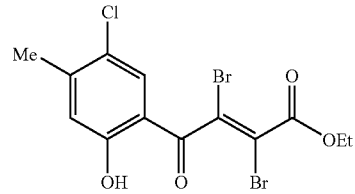

-continued

III-8

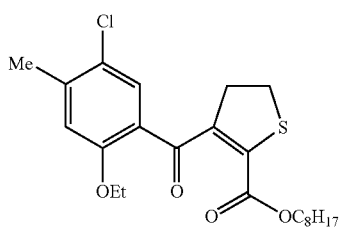

Example 68

Synthesis of (E)-4-(3-chloro-4-methoxyphenyl)-4-oxo-2-butenamide

Into a 500 ml four-neck flask were charged 66.9 g (0.682 mol) of maleic anhydride, 150 ml of chlorobenzene, 71.6 ml (0.546 mol) of diethyl sulfate under a nitrogen atmosphere. Then, the whole was cooled to 10° C. or lower and 67.6 g (0.507 mol) of aluminum chloride was added thereto. While temperature was maintained at 10 to 15° C., 23.2 ml (0.195 mol) of 1-chloro-2-methoxybenzene was added dropwise, followed by 4 hours of reaction. After termination of the reaction was confirmed by HPLC analysis, the reaction solution was added dropwise to 200 ml of a 1N hydrochloric acid aqueous solution cooled to 0° C. to decompose excess aluminum chloride. After liquid separation, the organic layer was washed with 200 ml of a 10% sodium bicarbonate aqueous solution to remove excess maleic anhydride. After the solvent was removed by evaporation under reduced pressure, the residue was treated with 200 ml of concentrated ammonia water for 1 hour while temperature was maintained at 0° C. and the resulting mixture was extracted with 200 ml of ethyl acetate. Then, the solvent was removed by evaporation under reduced pressure and the residue was crystallized from 5 ml of ethanol to obtain 23.9 g (yield 51.1%) of the aimed compound. As a result of HPLC analysis, the purity was found to be 99.2%.

Example 69

Synthesis of N-phenyl-(E)-4-(3-chloro-4-methoxyphenyl)-4-oxo-2-butenamide

Into a 500 ml four-neck flask were charged 66.9 g (0.682 mol) of maleic anhydride, 150 ml of chlorobenzene, 71.6 ml (0.546 mol) of diethyl sulfate, and 0.186 g (0.975 mmol) of copper iodide under a nitrogen atmosphere. Then, the whole was cooled to 10° C. or lower and 67.6 g (0.507 mol) of aluminum chloride was added thereto. While temperature was maintained at 10 to 15° C., 23.2 ml (0.195 mol) of 1-chloro-2-methoxybenzene was added dropwise, followed by 2 hours of reaction. After termination of the reaction was confirmed by HPLC analysis, the reaction solution was added dropwise to 200 ml of a 1N hydrochloric acid aqueous solution cooled to 0° C. to decompose excess aluminum chloride. After liquid separation, the organic layer was washed with 200 ml of a 10% sodium bicarbonate aqueous solution to remove excess maleic anhydride. Then, 13.3 g (0.143 mol) of aniline was added to the organic layer, followed by 4 hours of reflux while ethanol formed during the reaction was removed. After completion of the reaction, the solvent was removed by evaporation under reduced pressure and the residue was crystallized from 10 ml of ethanol to obtain 32.3 g (yield 52.5%) of the aimed compound. As a result of HPLC analysis, the purity was found to be 99.1%.

Example 70

Synthesis of (E)-4-(3-chloro-4-methoxyphenyl)-4-oxo-2-butenoic acid

Into a 500 ml four-neck flask were charged 66.9 g (0.682 mol) of maleic anhydride, 150 ml of chlorobenzene, and 71.6 ml (0.546 mol) of diethyl sulfate under a nitrogen atmosphere. Then, the whole was cooled to 10° C. or lower and 67.6 g (0.507 mol) of aluminum chloride was added thereto. While temperature was maintained at 10 to 15° C., 23.2 ml (0.195 mol) of 1-chloro-2-methoxybenzene was added dropwise, followed by 4 hours of reaction. After termination of the reaction was confirmed by HPLC analysis, the reaction solution was added dropwise to 200 ml of a 1N hydrochloric acid aqueous solution cooled to 0° C. to decompose excess aluminum chloride. After liquid separation, the organic layer was washed with 200 ml of a 10% sodium bicarbonate aqueous solution to remove excess maleic anhydride. Then, 42.9 g (0.286 mol) of sodium iodide and 31.1 g (0.286 mol) of chlorotrimethylsilane were added to the organic layer, followed by heating and refluxing. After completion of the reaction, the organic layer was washed with 100 ml of a 5% sodium thiosulfate aqueous solution and 100 ml of a saturated sodium hydrogen carbonate aqueous solution to extract (E)-4-(3,4-dimethoxyphenyl)-4-oxo-2-butenoic acid into the aqueous layer, followed by adjusting the aqueous layer to pH 2.0. After 24 h of stirring at 5° C., filtration was conducted to obtain 21.1 g (yield 45.0%) of the aimed compound as light yellow crystals. As a result of HPLC analysis, the purity was found to be 99.1%.

Example 71

Synthesis of (E)-1-(3-chloro-4-methoxyphenyl)-4-phenyl-2-butene-1,4-dione

Into a 200 ml four-neck flask were added 10 g (0.038 mol) of ethyl (E)-4-(3-chloro-4-methoxyphenyl)-4-oxo-2-butenoate obtained in Example 3 and 50 ml of tetrahydrofuran under a nitrogen atmosphere, and 22.5 ml (0.045 mol) of a tetrahydrofuran solution of 32% phenylmagnesium bromide was slowly added dropwise so as to maintain inner temperature at 10° C. or lower. Then, after 1 hour of stirring at room temperature, the whole was again cooled and 50 ml of a 5% ammonium chloride aqueous solution was added thereto. After liquid separation, the resulting organic layer was washed with 50 ml of a 10% sodium bicarbonate aqueous solution and then with 50 ml of water. After the solvent was removed by evaporation under reduced pressure, the residue was crystallized from 10 ml of ethanol to obtain 8.9 g (yield 78.0%) of the aimed compound. As a result of HPLC analysis, the purity was found to be 99.3%.

Example 72

Synthesis of (E)-4-(3,4-dimethoxyphenyl)-4-oxo-2-butenamide

Into a 500 ml four-neck flask were charged 66.9 g (0.682 mol) of maleic anhydride, 150 ml of chlorobenzene, 71.6 ml (0.546 mol) of diethyl sulfate, and 0.186 g (0.975 mmol) of copper iodide under a nitrogen atmosphere. Then, the whole was cooled to 10° C. or lower and 67.6 g (0.507 mol) of aluminum chloride was added thereto. While temperature was maintained at 10 to 15° C., 25 ml (0.195 mol) of 1,2-dimethoxybenzene was added dropwise, followed by 2 hours of reaction. After termination of the reaction was confirmed by HPLC analysis, the reaction solution was added dropwise to 200 ml of a 1N hydrochloric acid aqueous solution cooled to 0° C. to decompose excess aluminum chloride. After liquid separation, the organic layer was washed with 200 ml of a 10% sodium bicarbonate aqueous solution to remove excess maleic anhydride. After the solvent was removed by evaporation under reduced pressure, the residue was treated with 200 ml of concentrated ammonia water for 1 hour while temperature was maintained at 0° C. and the resulting mixture was extracted with 200 ml of ethyl acetate. Then, the solvent was removed by evaporation under reduced pressure and the residue was crystallized from 5 ml of ethanol to obtain 28.9 g (yield 63.2%) of the aimed compound. As a result of HPLC analysis, the purity was found to be 99.1%.

Example 73

Synthesis of N-phenyl-(E)-4-(3,4-dimethoxyphenyl)-4-oxo-2-butenamide

Into a 500 ml four-neck flask were charged 66.9 g (0.682 mol) of maleic anhydride, 150 ml of chlorobenzene, and 71.6 ml (0.546 mol) of diethyl sulfate under a nitrogen atmosphere. Then, the whole was cooled to 10° C. or lower and 67.6 g (0.507 mol) of aluminum chloride was added thereto. While temperature was maintained at 10 to 15° C., 25 ml (0.195 mol) of 1,2-dimethoxybenzene was added dropwise, followed by 4 hours of reaction. After termination of the reaction was confirmed by HPLC analysis, the reaction solution was added dropwise to 200 ml of a 1N hydrochloric acid aqueous solution cooled to 0° C. to decompose excess aluminum chloride. After liquid separation, the organic layer was washed with 200 ml of a 10% sodium bicarbonate aqueous solution to remove excess maleic anhydride. Then, 13.3 g (0.143 mol) of aniline was added, followed by 4 hours of refluxing while removing ethanol formed during the reaction. After completion of the reaction, the solvent was removed under reduced pressure and the residue was crystallized from 10 ml of ethanol to obtain 34.8 g (yield 57.4%) of the aimed compound. As a result of HPLC analysis, the purity was found to be 99.0%.

Example 74

Synthesis of (E)-4-(3,4-dimethoxyphenyl)-4-oxo-2-butenoic acid

Into a 500 ml four-neck flask were charged 66.9 g (0.682 mol) of maleic anhydride, 150 ml of chlorobenzene, 71.6 ml (0.546 mol) of diethyl sulfate, and 0.186 g (0.975 mmol) of copper iodide under a nitrogen atmosphere. Then, the whole was cooled to 10° C. or lower and 67.6 g (0.507 mol) of aluminum chloride was added thereto. While temperature was maintained at 10 to 15° C., 25 ml (0.195 mol) of 1,2-dimethoxybenzene was added dropwise, followed by 2 hours of reaction. After termination of the reaction was confirmed by HPLC analysis, the reaction solution was added dropwise to 200 ml of a 1N hydrochloric acid aqueous solution cooled to 0° C. to decompose excess aluminum chloride. After liquid separation, the organic layer was washed with 200 ml of a 10% sodium bicarbonate aqueous solution to remove excess maleic anhydride. Then, 42.9 g (0.286 mol) of sodium iodide and 31.1 g (0.286 mol) of chlorotrimethylsilane were added to the organic layer, followed by heating and refluxing. After completion of the reaction, the organic layer was washed with 100 ml of a 5% sodium thiosulfate aqueous solution and 100 ml of a saturated sodium hydrogen carbonate aqueous solution to extract (E)-4-(3,4-dimethoxyphenyl)-4-oxo-2-butenoic acid into the aqueous layer, followed by adjusting the aqueous layer to pH 2.0. After 24 h of stirring at 5° C., filtration was conducted to obtain 24.9 g (yield 54.2%) of the aimed compound as light yellow crystals. As a result of HPLC analysis, the purity was found to be 98.5%.

Example 75

Synthesis of (E)-1-(3,4-dimethoxyphenyl)-4-phenyl-2-butene-1,4-dione

Into a 200 ml four-neck flask were added 10 g (0.038 mol) of ethyl (E)-4-(3,4-dimethoxyphenyl)-4-oxo-2-butenoate obtained in Example 1 and 50 ml of tetrahydrofuran under a nitrogen atmosphere, and 22.5 ml (0.045 mol) of a tetrahydrofuran solution of 32% phenylmagnesium bromide was slowly added dropwise so as to maintain inner temperature at 10° C. or lower. Then, after 1 hour of stirring at room temperature, the whole was again cooled and 50 ml of a 5% ammonium chloride aqueous solution was added to effect hydrolysis. After liquid separation, the resulting organic layer after completion of the reaction was washed with 50 ml of a 10% sodium bicarbonate aqueous solution and then with 50 ml of water. After the solvent was removed by evaporation under reduced pressure, the residue was crystallized from 10 ml of ethanol to obtain 8.8 g (yield 78.0%) of the aimed compound. As a result of HPLC analysis, the purity was found to be 99.2%.

INDUSTRIAL APPLICABILITY

According to the process of the invention, it is possible to stably supply a 4-phenyl-4-oxo-2-butenoate derivative useful as an intermediate for medicines, pesticides, perfumes, and the like, in a short period of time, at low cost, in high purity and on an industrial scale, and thus the process has industrially extremely high practical use.

The invention claimed is:
1. A process for producing a 4-phenyl-4-oxo-2-butenoate derivative represented by the following general formula (III) or (IV), which comprises simultaneously or continuously reacting an aromatic hydrocarbon represented by the following general formula (I) and a maleic anhydride derivative represented by the following general formula (II) in the presence of an acid catalyst and an alkylating agent wherein the alkylating agent is a sulfuric ester

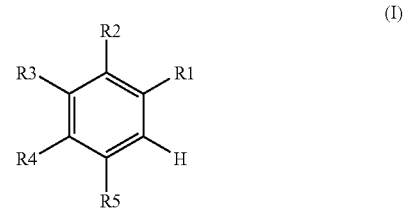

wherein R1 to R5 each independently represents a hydrogen atom, an electron-donating group, or an electron-withdrawing group, and adjacent groups of R1 to R5 may be combined to form a ring;

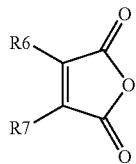
(II)

wherein R6 or R7 each independently represents a hydrogen atom, an alkyl group, an alkenyl group, an alkynyl group, an aryl group, an alkoxy group, an aryloxy group, a carbonyl group, a sulfonyl group, a carbonyloxy group, a carbonylamino group, a sulfonylamino group, an amino group, a cyano group, an alkylthio group, an arylthio group, a heterocyclic residual group, or a halogen atom, and R6 and R7 may be combined to form a partially saturated ring, an aromatic ring, or a heterocyle;

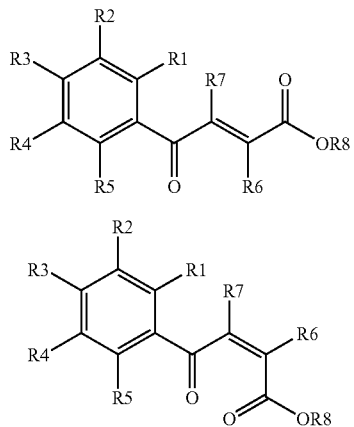
(III)

(IV)

wherein R1 to R7 have the same meanings as above and R8 represents an alkyl group.

2. The process for producing the 4-phenyl-4-oxo-2-butenoate derivative according to claim 1, wherein R1 to R5 in the above general formula (I) each independently is a hydrogen atom or an electron-donating group.

3. The process for producing the 4-phenyl-4-oxo-2-butenoate derivative according to claim 1, wherein the above general formula (I) has at least one electron-donating group and at least one electron-withdrawing group, and the total of Hammett's substituent constant σ values of R1 to R5 is 0 or more.

4. The process for producing the 4-phenyl-4-oxo-2-butenoate derivative according to claim 1, wherein the electron-donating group of R1 to R5 in the above general formula (I) is a group chosen from alkoxy, alkylthio, monosubstituted amino, and disubstituted amino.

5. The process for producing the 4-phenyl-4-oxo-2-butenoate derivative according to claim 1, wherein the acid catalyst is aluminum chloride.

6. The process for producing the 4-phenyl-4-oxo-2-butenoate derivative according to claim 1, which is used for producing a 4-phenyl-2-butene-1,4-dione derivative represented by the following general formula (V) or (VI):

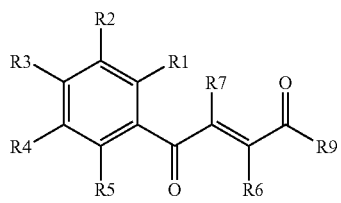
(V)

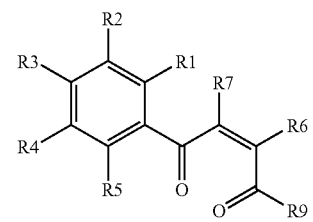
(VI)

wherein R1 to R7 have the same meanings as above and R9 represents a hydrogen atom, an alkyl group, an aryl group, a hydroxyl group, an amino group, or a hydroxylamino group.

* * * * *